United States Patent [19]

Auer

[11] 4,257,106
[45] Mar. 17, 1981

[54] METHOD AND APPARATUS FOR THERMAL IMAGING

[75] Inventor: Siegfried O. Auer, Bowie, Md.

[73] Assignee: Norlin Industries, Inc., Deerfield, Ill.

[21] Appl. No.: 42,112

[22] Filed: May 24, 1979

[51] Int. Cl.³ .............................................. G01J 4/00
[52] U.S. Cl. .................................... 364/525; 364/516;
356/369; 250/338
[58] Field of Search ............... 364/525, 514, 515, 516,
364/517; 356/72, 73, 445, 369, 51; 250/338, 340

[56] References Cited

U.S. PATENT DOCUMENTS

| 3,390,605 | 7/1968 | Nagamura | 356/73 |
|---|---|---|---|
| 3,631,254 | 12/1971 | Covault | 250/340 |
| 3,784,307 | 1/1974 | Jackson et al. | 250/340 |
| 3,802,778 | 4/1974 | Newburgh | 356/369 |
| 3,807,868 | 4/1974 | Simila | 356/369 |
| 3,994,586 | 11/1976 | Sharkins et al. | 356/51 |
| 4,053,232 | 10/1977 | Dill et al. | 356/369 |
| 4,129,781 | 12/1978 | Doyle | 250/338 |

OTHER PUBLICATIONS

"Zur Theorie Der Diffusen Lichtreflexion", Z. Physik, vol. 30, pp. 66-72, (1924), by G. I. Pokrowski.
"Analysis of Light Scattered From A Surface of Low Gloss into its Specular and Diffuse Components", Proc. Physical Soc'y of London, vol. 51, pp. 274-295, (1939), by W. W. Barkas.
"Average Irregularity Representation of a Rough Surface for Ray Reflection", J. Optical Soc'y of America, vol. 65, pp. 531-536, (1975), by Trowbridge & Reitz.

Primary Examiner—Charles E. Atkinson
Assistant Examiner—Gary Chin
Attorney, Agent, or Firm—Jack Kail; Ronald J. Kransdorf

[57] ABSTRACT

A method of daytime imaging in a range of thermal wavelengths (3-5 microns) which includes specularly reflected solar radiation. Mathematical processing serves to separate the thermal and specular reflection components based on Fresnel's equations which relate the thermal component to three variables: the total radiation intensity; the degree of polarization of the total radiation; and the degree of polarization of the specular reflection component. The first two of these variables may be measured by means of a photometer which is scanned across a target area, and a suitably oriented polarizing filter. The third variable can be calculated as a function of two other quantities: the angle of incidence of sunlight on the target object and the index of refraction of the target object. The first of these two quantities is calculable from time and geographical position data, while the second can be estimated with sufficient accuracy. Each calculation produces a single pixel, and a succession of such pixels is used to build up an image upon a CRT raster which is synchronized with the photometer scan.

4 Claims, 5 Drawing Figures

METHOD AND APPARATUS FOR THERMAL IMAGING

This invention relates generally to thermal (infra-red) imaging, and in particular, to the problems encountered when such imaging is performed in daylight at wavelengths which include specularly reflected sunligth.

BACKGROUND AND PRIOR ART

Thermal imaging is the art of photographing an object in the infra-red portion of the spectrum, by sensing the thermal radiation which is supplied by the object itself. Some applications of thermal imaging do not need to take into account the transmissivity of the atmosphere or the presence of noise caused by specularly reflected infra-red radiation from the sun. Applications such as detecting heat leaks in an inadequately insulated home, nondestructive testing of materials, engine analyses, or body scanning for medical diagnostic purposes all fall into this category because they can either be performed indoors or at night, so that sunlight is not a complicating factor, or they can be performed at such close range that high atmospheric transmissivity is not required. But other applications, principally those involving airborne or satellite imaging, must be conducted outdoors and at a wavelength capable of penetrating a substantial intervening thickness of atmosphere. These applications include military reconnaissance to locate camouflaged enemy operations, and surveys to identify stressed plants, predict crop yield, detect forest fires, perform wildlife inventories, estimate soil moisture and evaporation rates, or measure thermal inertia of geologic rock formations.

There are only two "windows" in the transmission spectrum of the atmosphere in which thermal imaging from aircraft or space is feasible. One is the wavelength band from 3 to 5 $\mu$m and the other is the wavelength band from 8 to 13 $\mu$m. High sensitivity in the 8–13 $\mu$m band can only be achieved with cryogenically cooled detectors, such as Hg-Cd-Te material operating at 77° K. Thermoelectric cooling is not sufficient to reach such low temperatures. Therefore, sensitive thermal imaging in the 8–13 $\mu$m band always requires a supply of liquid nitrogen to be carried in bulky and heavy Dewar containers as part of the imaging equipment. In addition, certain precautions are necessary because of the hazards associated with liquid nitrogen. Also, a user in a remote place is forced either to carry along a large extra reservoir of liquid nitrogen, or to travel regularly to a distant source to replenish the supply.

Sensitive thermal imaging in the 3–5 $\mu$m band, on the other hand, is possible without the use of liquid nitrogen. Cooling of the detector (such as PbSe) is necessary to some degree, but only down to 195° K., which can be reached using a thermo-electric cooler. Thermal imaging in this band at night has been done successfully. But during the day, such thermal imaging is severely disturbed by the presence of specularly reflected sunlight of the same wavelength.

The purpose of this invention is to provide instrumentation that is capable of analyzing radiation outgoing from the object into two components, the reflected sunlight component and the thermal emission component, in order to record high-quality thermal images in bright sunlight, while using only light-weight, electronically cooled equipment.

What is needed to accomplish this objective is some way of discriminating specularly reflected sunlight from thermal radiation, when both are in the 3–5 $\mu$m wavelength band. Techniques have been described in the literature for discriminating between two different kinds of radiation, specular and diffuse, the basis of the discrimination being a difference in degree of polarization. But until now it appears that no one has devised a way of separating thermal from reflected radiation. The work described in the literature, moreover, has been confined to the visible portion of the spectrum, where there is no significant amount of thermal radiation at ordinary temperatures.

BRIEF SUMMARY OF THE INVENTION

The basis for discriminating between the thermal and reflected components of total incident radiation resides in the fact that the reflected component is highly polarized, while the thermal component is essentially unpolarized. From Fresnel's equations it is possible to calculate the thermal component as a function of three variables: the total radiation intensity, the degree of polarization of the total radiation (both of which can be measured by a photometer), and the degree of polarization of the reflected component. The latter variable in turn can be calculated as a function of two other variables: the angle of incidence of sunlight upon the target object, and the index of refraction of the target object. The first of these can be calculated from time and geographical position data (thus fixing the position of the sun, which determines the angle of incidence of sunlight). The second quantity varies relatively little for such a broad range of possible target objects that it can be safely estimated. The end result of these calculations is the brightness, in thermal radiation at 3–5 $\mu$m, of a single target element sensed by the photometer. If the photometer is scanned over an area comprising many such target elements, each of the elements comprises a pixel, and all the pixels together form an image. Then a conventional cathode ray tube, the raster of which is synchronized with the photometer scan, can be used to construct the thermal image if the brightness input signal is taken from the output of the thermal brightness calculation. The reflected sunlight is effectively excluded from the constructed image, even though it is an important component of the raw signal detected by the photometer, and is at the same wavelength as the thermal component.

DETAILED DESCRIPTION OF THE DRAWINGS

The invention thus generally indicated will now be described in detail in connection with the illustrative embodiments represented by the following drawings.

DETAILED DESCRIPTION OF THE PREFERRED EMBODIMENT

The scanning technique of thermal photometry is generally known, and need not be described here. Reference is made to handbooks such as "Fundamentals of Remote Sensing", edited by W. G. Collins and J. L. vanGenderen (1974).

Each molecule in an object at any temperature above 0° K. radiates unpolarized light in all directions. When this radiation strikes a surface facet upon emerging from the interior of the object, one portion of it is reflected back into the object, while the remaining portion is refracted out of the object into the surrounding medium, usually air. Both the reflected and retracted portions of any given ray are generally polarized. The relative intensities of these portions and their degrees of polarization follow from Fresnel's equations, depending only on the angle of incidence of the beam on the surface facet and on the index of refraction of the surface material. When the surface is rough, the orientations of the planes of polarization of individual refracted rays are practically random, due to the randomness of the orientation of the surface facets. Thus the superposition of all randomly polarized rays emerging in a given direction is practically unpolarized radiation.

Figure 1:
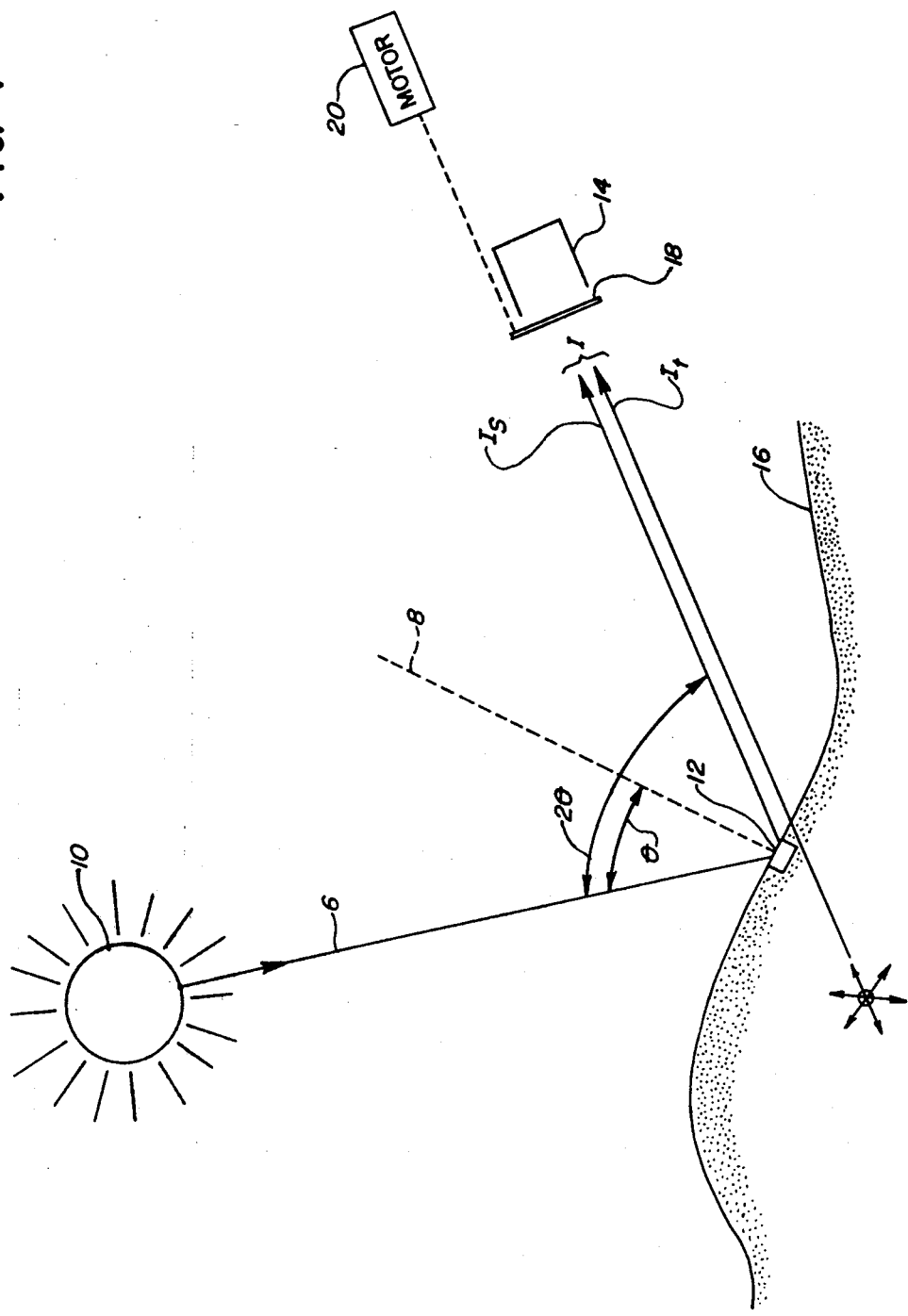
FIG. 1 is a diagram showing the origin of both the thermal and reflected radiation components sensed by an airborne or satellite-borne photometer.

With reference to FIG. 1, a ray of sunlight 6 is reflected into a given direction of observation only from a surface facet 12 whose normal coincides with the bisector 8 of the angle $2\theta$ formed by the sun 10, the object surface facet element 12, and the photometer 14. All other facets of the object surface 16 reflect sunlight into different directions which are not observed by the photometer 14. The reflected ray $I_s$ is generally polarized. The intensities of its components perpendicular ($I_{s\perp}$) and parallel ($I_{s\parallel}$) to the plane of incidence (i.e., the plane which contains the sun 10, the object facet 12, and the photometer 14) depend on the angle of incidence $\theta$ (which is half the angle "sun-object-photometer"=$2\theta$), and on the index of refraction n of the surface material. According to Fresnel's equations:

$$I_{s\perp} = \left[\frac{\cos\theta - (n^2 - \sin^2\theta)^{\frac{1}{2}}}{\cos\theta + (n^2 - \sin^2\theta)^{\frac{1}{2}}}\right]^2 \frac{I_o}{2} \quad \text{(equation 1)}$$

$$I_{s\parallel} = \left[\frac{n^2\cos\theta - (n^2 - \sin^2\theta)^{\frac{1}{2}}}{n^2\cos\theta + (n^2 - \sin^2\theta)^{\frac{1}{2}}}\right]^2 \frac{I_o}{2} \quad \text{(equation 2)}$$

where $I_o$ is the intensity of unpolarized incident sunlight (ray 6). The degree of polarization of the reflected sunlight, $$P_s = \frac{I_{s\perp} - I_{s\parallel}}{I_{s\perp} + I_{s\parallel}}$$

can be expressed in terms of $\theta$ and n as follows:

$$P_s = \frac{\left[\frac{\cos\theta - (n^2 - \sin^2\theta)^{\frac{1}{2}}}{\cos\theta + (n^2 - \sin^2\theta)^{\frac{1}{2}}}\right]^2 - \left[\frac{n^2\cos\theta - (n^2 - \sin^2\theta)^{\frac{1}{2}}}{n^2\cos\theta + (n^2 - \sin^2\theta)^{\frac{1}{2}}}\right]^2}{\left[\frac{\cos\theta - (n^2 - \sin^2\theta)^{\frac{1}{2}}}{\cos\theta + (n^2 - \sin^2\theta)^{\frac{1}{2}}}\right]^2 + \left[\frac{n^2\cos\theta - (n^2 - \sin^2\theta)^{\frac{1}{2}}}{n^2\cos\theta + (n^2 - \sin^2\theta)^{\frac{1}{2}}}\right]^2} \quad \text{(equation 3)}$$

Note that at the Brewster angle, $\theta_B$=arc tan n, the component $I_{s\parallel}$ varnishes while $I_{s\perp}\neq 0$, and thus the reflected light is completely polarized ($P_s$=1.00), except that if n is a complex number (due to absorption), then, at $\theta_B$, $I_{s\parallel}$ has a minimum and $P_s$ has a maximum.

The portion of sunlight 6 which is not reflected from the surface will be refracted into the object 12. There it will be absorbed, heating the object, or (if the absorption coefficient is small) a portion will be refracted back out through the surface, usually after having undergone many internal reflections at randomly oriented angles. In the latter case, the re-emitted sunlight will be practically unpolarized and it will somewhat-enhance the intensity of the unpolarized thermal radiation from the object. In the first case (which is the normal case) it will not add to the brightness of the thermal radiation.

The detection problem here has a superficial similarity to the problem of separating the specular (at-the-surface) reflection component from the diffuse (subsurface) reflection component which Pokrowski and others have studied since 1924 (Z. Physik vol. 30, pp. 66–72). But in the present case we have two different sources of the radiation, an external reflected one and an internal thermal one (with different spectral characteristics); and the mathematical treatment is significantly different.

What is actually observed in a given direction is a superposition I (see FIG. 1), of the virtually unpolarized thermal radiation $I_t$ coming from inside, and the polarized reflected sunlight $I_s$ coming from the surface 12:

$$I = I_t + I_s.$$

For any given configuration of sun-object-photometer, the angle $\theta$ is known. For any given object, the index of refraction n is also known or its value can be estimated. Therefore, the degree of polarization $P_s$ of the reflected sunlight can be calculated using Eq. (3) above. The required polarization components of $I_s$ are given in Eqs. (1) and (2) above, and $$I_s = I_{s\perp} + I_{s\parallel}.$$

Since $I_t$ is virtually unpolarized, $$I_{t\perp} = I_{t\parallel} = 0.5\, I_t.$$

The components of the total light I are $$I_\perp = I_{t\perp} + I_{s\perp} = 0.5\, I_t + I_{s\perp} \quad \text{(equation 4)}$$

$$I_\parallel = I_{t\parallel} + I_{s\parallel} = 0.5\, I_t + I_{s\parallel} \quad \text{(equation 5)}$$

The degree of polarization of I $$\begin{aligned}
P &= \frac{I_\perp - I_\parallel}{I_\perp + I_\parallel} \quad \text{(equation 6)}\\
&= \frac{0.5\, I_t + I_{s\perp} - 0.5\, I_t - I_{s\parallel}}{0.5\, I_t + I_{s\perp} + 0.5\, I_t + I_{s\parallel}}\\
&= \frac{I_{s\perp} - I_{s\parallel}}{I_t + I_{s\perp} + I_{s\parallel}}\\
&= \frac{P_s(I_{s\perp} + I_{s\parallel})}{I_t + (I_{s\perp} + I_{s\parallel})}\\
&= P_s\frac{I_s}{I_t + I_s}. \quad \text{(equation 7)}
\end{aligned}$$

Rearranging gives $$I_s = I\, P/P_s \quad \text{(equation 8)}$$

and $$I_t = I - I_s = I\,(1 - P/P_s). \quad \text{(equation 9)}$$

While I and P are the intensity and degree of polarization, respectively, of the actually measurable outgoing radiation, $P_s$ can be calculated from Eq. (3). Thus, $I_s$ and $I_t$ can be completely determined.

Although the index of refraction n usually has to be estimated, $P_s(\theta, n)$ is not very sensitive to small uncertainties in n, particularly when $\theta$ is near the Brewster angle. The following table lists values of $P_s$ for a number of combinations of $\theta$ (45°, 50°, ... 80°) and n (1.3, 1.35, 1.4, ... 2.0).

| n ↓ | θ → 45° | 50° | 55° | 60° | 65° | 70° | 75° | 80° |
|---|---|---|---|---|---|---|---|---|
| 1.3 | 0.9129 | 0.9903 | 0..9892 | 0.9118 | 0.7797 | 0.6207 | 0.4561 | 0.297 |
| 1.35 | 0.8924 | 0.9809 | 0.9963 | 0.9351 | 0.8139 | 0.6581 | 0.4897 | 0.3219 |
| 1.4 | 0.8718 | 0.9696 | 0.9996 | 0.9538 | 0.8437 | 0.6921 | 0.5211 | 0.3454 |
| 1.45 | 0.8515 | 0.9569 | 0.9997 | 0.9685 | 0.8697 | 0.7232 | 0.5504 | 0.3678 |
| 1.5 | 0.8315 | 0.9432 | 0.9974 | 0.9798 | 0.8924 | 0.7516 | 0.5781 | 0.3892 |
| 1.55 | 0.8119 | 0.9287 | 0.9931 | 0.9882 | 0.9121 | 0.7776 | 0.6042 | 0.4098 |
| 1.6 | 0.7929 | 0.9138 | 0.9872 | 0.9941 | 0.9292 | 0.8015 | 0.6289 | 0.4297 |
| 1.65 | 0.7744 | 0.8987 | 0.9799 | 0.9978 | 0.9438 | 0.8234 | 0.6523 | 0.4489 |
| 1.7 | 0.7565 | 0.8834 | 0.9715 | 0.9997 | 0.9563 | 0.8435 | 0.6745 | 0.4674 |
| 1.75 | 0.7392 | 0.8682 | 0.9623 | 0.9999 | 0.9669 | 0.8618 | 0.6956 | 0.4855 |
| 1.8 | 0.7225 | 0.853 | 0.9524 | 0.9987 | 0.9757 | 0.8786 | 0.7156 | 0.5029 |
| 1.85 | 0.7064 | 0.838 | 0.942 | 0.9963 | 0.9828 | 0.8939 | 0.7346 | 0.5199 |
| 1.9 | 0.6909 | 0.8232 | 0.9312 | 0.9928 | 0.9886 | 0.9078 | 0.7527 | 0.5364 |
| 1.95 | 0.6559 | 0.8086 | 0.9201 | 0.9885 | 0.993 | 0.9205 | 0.7698 | 0.5525 |
| 2 | 0.6614 | 0.7943 | 0.9088 | 0.9833 | 0.9963 | 0.9319 | 0.7861 | 0.5682 |

Degree of polarization as function of angle of incidence $\theta$ and of index of refraction n.

It can be seen that for $\theta = 55°$ and for a range of n from 1.3 to 1.6, the degree of polarization is very close to 1.00. In the 3–5 μm wavelength band, the indices of refraction of most if not all plant surface materials and of water have been found to be in the range of 1.33–1.48. Furthermore, the angle of observation can be controlled by placement of the photometer 14 so that $\theta$ is in the neighborhood of 55° (i.e. near the Brewster angle) during the times when reflected sunlight is a problem. Thus, it appears safe to assume an average of n=1.39 for all plant canopies or other materials on the earth's surface which contain a substantial amount of water, without risking significant uncertainties in the calculated results.

Figure 2A:
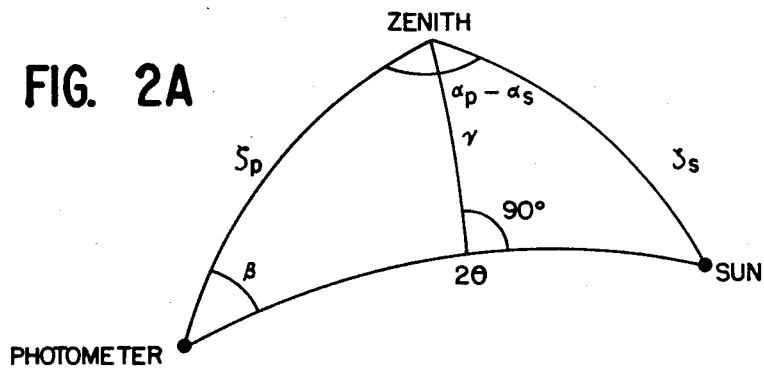
FIG. 2A is a reproduction of a selected portion of FIG. 2, isolated for clarity.
Figure 2:
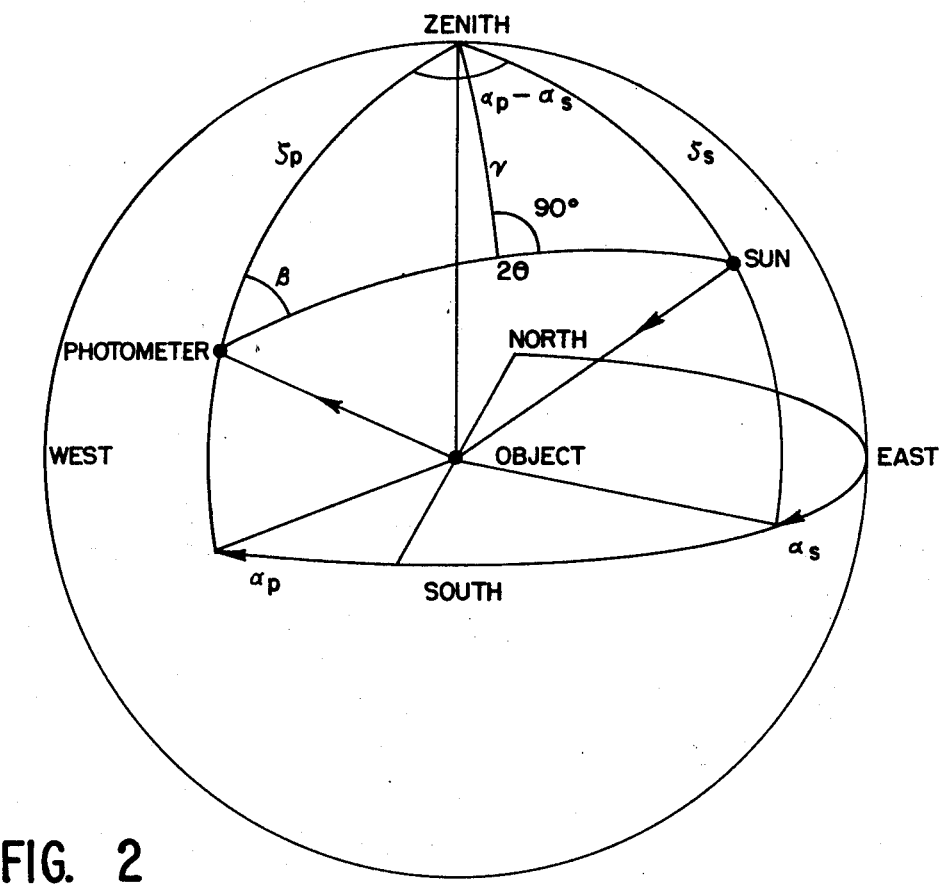
FIG. 2 shows the spherical trigonometric configuration assumed by the photometer, the object and the sun during such photometric observation.

To compute the angle $\theta$, one needs the date (D=day of year) and the time (t=Greenwich mean time in hours) which comes from an accurate calendar-clock. One also needs the local geographic coordinates ($\phi$=geographic latitude and $\eta$=geographic longitude) which are stored in a programmable read-only memory (PROM). With reference to FIGS. 2 and 2A, the sun hour h angle (in degrees) is $$h = 15t + \eta - 180 \quad \text{(equation 10)}$$

The sun's declination $\delta$ (in degrees) is approximately $$\delta = 23.45 \sin[360(D-80)/365]. \quad \text{(equation 11)}$$

The sun zenith angle $\zeta_s$ (see FIG. 2) is $$\zeta_s = \arccos(\sin\phi \sin\delta + \cos\phi \cos\delta \cos h). \quad \text{(equation 12)}$$

The sun azimuth angle $\alpha_s$ is $$\alpha_s = \arccos[(\sin\phi \cos\zeta_s - \sin\delta)/(\cos\phi \sin\zeta_s)]. \quad \text{(equation 13)}$$

To eliminate ambiguities about the sign of $\alpha_s$, the following equation must be used in addition to Eq. 13:

$$\alpha_s = \arcsin(\cos\delta \sin h / \sin\zeta_s). \quad \text{(equation 14)}$$

The absolute values $|\alpha_s|$ from both Eqs. 13 and 14 are identical. Zenith angles are measured from the zenith to the sun; azimuth angles are measured from North ($\alpha_s=0$), over East ($\alpha_s=90°$), South ($\alpha_s=180°$), West ($\alpha_s=270°$) to the projection of the sun on the horizon.

The view direction of the photometer is given by the view zenith $\zeta_p$ and the view azimuth $\alpha_p$. The latter is the angle between due North and the projection of the view axis on the horizontal plane; it is automatically measured and recorded. $\zeta_p$ is the angle between a vertical line and the view axis of the photometer. It is automatically measured, too, and stored for use in the calculations.

To obtain the angle of incidence $\theta$, one solves the following equation:

$$\theta = 0.5 \arccos[\cos\zeta_p \cos\zeta_s + \sin\zeta_s \sin\zeta_p \cos(\alpha_p - \alpha_s)]. \quad \text{(equation 15)}$$

Having determined $\theta$ and knowing n, the degree of polarization of the reflected sunlight component $P_s$ can be calculated from Eq. 3.

For obtaining the degree of polarization, P, of the total received light I, (reflected sunlight $I_s$ and thermal radiation $I_t$ of the object combined), the linear polarization components whose electric field vectors vibrate parallel ($I_\parallel$, minimum brightness component) and perpendicular ($I_\perp$, maximum brightness component) to the plane of incidence, have to be measured separately. One of two methods can be used, both employing a linear polarizer, for example a wire grid polarizer on a silver bromide substrate manufactured by Perkin-Elmer of Norwalk, Conn., or its equivalent.

In the first method, the polarizer 18 (see FIG. 1) is placed in front of the aperture of the photometer 14 and rotated about the view axis (line of sight), while brightness is recorded continuously. Within each 180° rotation, there should be observed the maximum ($I_\perp$) and the minimum ($I_\parallel$) brightness, which are electronically extracted from among all recorded values and entered in Eq. 6.

In the second method, the same arrangement is used, but the polarizer 18 is rotated by a precalculated angle such that its direction of transmission is in the plane of incidence (for measuring $I_\perp$) or perpendicular to it (for measuring $I_\parallel$). The rotation angle can be expressed by referencing it either to the vertical direction or to the vertical plane which contains the line of sight.

In the second method, the angle $\beta$ (see FIG. 2) is the angle between the plane of incidence and the vertical plane containing the line of sight:

$$\beta = \arcsin[\sin(\alpha_p - \alpha_s)/\sin 2\theta]. \quad \text{(equation 16)}$$

In the first method, the angle $\gamma$ (see FIG. 2) is the angle between the plane of incidence and the vertical direction:

$$\gamma = \arcsin(\sin \zeta_p \sin \beta). \quad \text{(equation 17)}$$

One then calculates either $\beta$ or $\gamma$, depending on the most convenient technical solution, and then controls a motor 20 (FIG. 1) which rotates the polarizer 18 accordingly. The vertical direction reference is found from the normal of an artificial horizon. The vertical plane is found from the normal of an artifical horizon and from the direction of the optical axis.

Given the day and time of observation (digital output from a calender clock), the geographic latitude and longitude of the location, and the estimated index of refraction of the material of the object surface stored in a programmable read-only memory (PROM), a microprocessor can be programmed to properly orient the polarizer 18 and to calculate the thermal radiation from the object for any sun angle, sun brightness, and any look direction.

Figure 3:
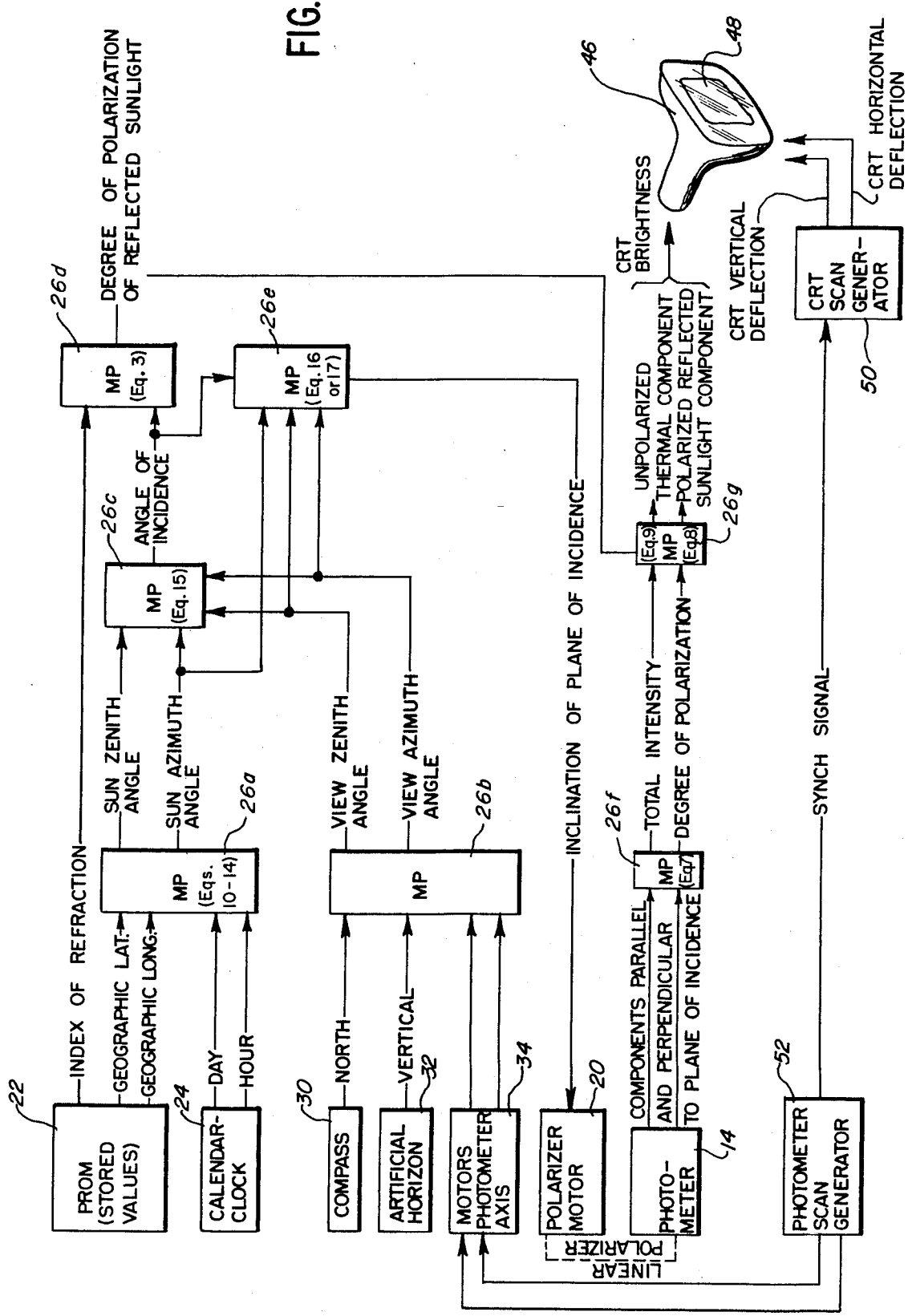
FIG. 3 is an electronic functional block diagram illustrating a thermal imaging device in accordance with this invention.

Thus, in FIG. 3, a programmable read-only memory (PROM) 22 stores values for the estimated index of refraction of the expected target objects, and for the geographic latitude and longitude of the place at which the imaging is being done at a given time. A calender-clock 24 continuously generates time and date information. A microprocessor 26 employs the geographical and time/date information to calculate the present sun angles, both zenith and azimuth. See Equations 10 through 14 above. (This aspect of microprocessor operation is schematically represented by functional block 26a. Other aspects of the operation of this very same microprocessor 26 are, for clarity of illustration, represented schematically by separate functional blocks 26b through 26g, as will be apparent from the subsequent discussion.) The microprocessor (block 26b) also receives orientation information from a compass 30, an artificial horizon device 32, and two photometer scan drive motors 34. Using this information, the microprocessor 26 derives the view angles, both zenith and azimuth. From the sun angles and view angles, the microprocessor (block 26c) calculates the angle of sunlight incidence (see Eq. 15). The microprocessor (block 26d) also employs that information, and the estimated index of refraction stored in the PROM 22, to calculate the degree of polarization of the reflected sunlight $I_s$ (see Eq. 3).

The angle of sunlight incidence is also used by the microprocessor (block 26e), along with the sun azimuth angle from block 26a and the view angles from block 26b, to calculate the inclination of the plane of incidence (Eq. 16 or 17). The latter quantity controls the motor 20 which rotates the linear polarizer 18 in front of the photometer 14. This permits the photometer to resolve the two components (parallel and perpendicular) of the received radiation I, which are then used by the microprocessor (block 26f) to calculate the total intensity $I = I_\perp + I_\parallel$ and the degree of polarization P (Eq. 7) of the received radiation. Using these two quantities, and the degree of polarization $P_s$ of reflected sunlight as calculated by block 26d, the microprocessor (block 26g) calculates the intensities of both the unpolarized thermal component $I_t$ (Eq. 9) and the polarized reflected component $I_s$ (Eq. 8) of the total received radiation I. One of these components, normally the thermal one $I_t$, is then used as the brightness signal to a cathode ray tube (CRT) 46 which generates an image upon a raster scan 48. The vertical and horizontal deflection signals for generating the CRT scan 48 some from a scan generator 50 which is synchronized with a circuit 52 which generates the photometer scan signals for the motors 34. As a result, the image on the CRT scan 48 is a picture of all the elements of target 16 as seen in the thermal radiation component $I_t$ only.

When a thermal image of an entire scene is to be generated, all computations have to be performed, in principle, on each individual image point (pixel). In practice, however, the time to record an entire image is usually on the order of a fraction of a second or minute; thus the sun's position and the geographical location (even when observation is made from a moving air- or spacecraft) is virtually constant. Also, if the angular diameter of the field of view is small ($\approx 1°$), average values for $\zeta_p$ and $\alpha_p$ can be used for all pixels. Under such simplifying conditions, Eqs. 10 through 17 and 3 need to be solved only once for one complete image. However, P has to be measured and Eq. 9 has to be solved for each individual pixel.

There is a reason for providing the polarized reflected sunlight ($I_s$) output from microprocessor block 26g as an alternative brightness signal input to the CRT. Solving Eq. 8 and using it to generate an image may be a useful tool to interpret a more complex thermal image. Areas not illuminated by the sun should be cooler than areas which are illuminated; if they are not, then the fact is significant.

An alternative embodiment of the invention is designed to take advantage of the special conditions which occur at the Brewster angle, $\theta_B$. Whenever the condition $\theta = \theta_B = \arctan n$ is met, totally specular reflection occurs, $P_s = 1$, and $I_{s\parallel} = 0$ for real values of n, as mentioned earlier. It follows from Eqs. 8 and 9 that $$I_s = PI \quad \text{(equation 18)}$$

$$I_t = (1 - P) I, \quad \text{(equation 19)}$$

and $$I_t = 2 I_\parallel \quad \text{(equation 20)}$$

Figure 4:
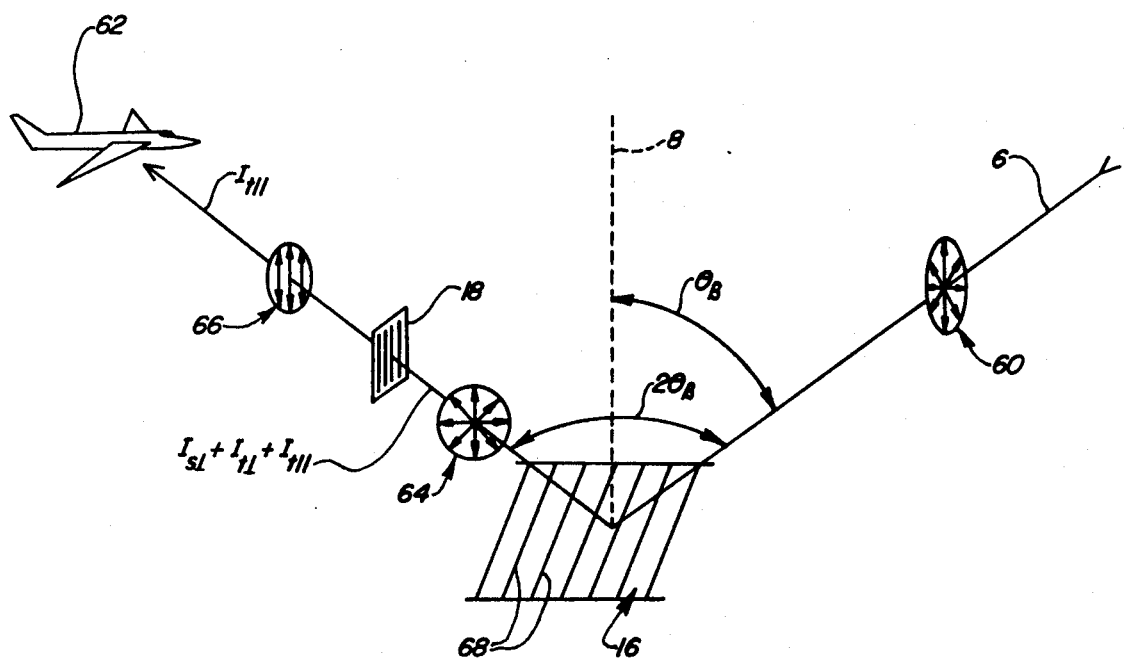
FIG. 4 is a diagram illustrating the operation of the device of FIG. 3 in one of several alternative modes.

Thus, under these conditions, only thermal radiation is being recorded when the axis of the polarizer 18 is oriented parallel to the plane of incidence of the sunlight. Since the recorded radiation $I_\parallel$ is exactly half the total thermal radiation $I_t$, thermal images can be generated immediately without the need to compute and subtract the reflected sunlight component. Observation at the Brewster angle can be done readily with an airborne scanner whose optical axis is held at the proper orientation with respect to the sun, while it is moving across the scene to be imaged, as indicated in FIG. 4.

In this embodiment of the invention, the beams of sunlight 6 incident upon the target are once again unpolarized (diagram 60). If these beams strike the target area 16 and are reflected over $2\theta_B$, twice the Brewster angle $\theta_B$, then the angles of incidence and reflection relative to the normal 8 are equal to the Brewster angle. Thus the rays $I_s$ reflected from target area 16 are totally polarized in the direction perpendicular to the plane of incidence (there is no parallel component). As a spacecraft or aircraft 62 flies over, the photometer 14 aboard the craft is maintained in an attitude such that it always sights along the path of reflection of one of these Brewster angle polarized beams $I_s$, which are now combined with whatever thermal radiation $I_t$ (both the parallel polarized component $I_{t\parallel}$ and the perpendicularly polarized component $I_{t\perp}$ thereof) happens to be incident along the reflection path. Thus, diagram 64 indicates that both polarization components (parallel and perpendicular) are initially present to some degree along the reflection path. But the parallel component is entirely thermal, not reflected. The linear polarizer 18 is then placed in front of the photometer on board the craft 62, and its polarization axis is held in the plane of incidence to screen out both of the perpendicular components $I_{s\perp}$ and $I_{t\perp}$. It thus gets rid of the reflected sunlight entirely, and leaves only one component (parallel) of the thermal radiation, as indicated by diagram 66. This single input $I_{t\parallel}$ to the photometer 14 permits the simplified calculations indicated above, as the photometer sweeps over scan lines 68 in the target area 16.

It will now be appreciated that this invention permits a thermal signal to be processed and extracted out of a great deal of specularly reflected noise when infra-red imaging is done during daylight hours in spectral regions which include sunlight; and that this is accomplished without the need for cryogenic cooling equipment and all the troubles which such equipment entails.

The embodiments disclosed are intended only to be exemplary, as the invention is no doubt capable of being practiced in a variety of different forms. Accordingly, the scope of protection is set forth only in the appended claims, which should be given a breadth of interpretation consistent with the novel teachings herein.

What is claimed is:

1. A device for daytime measurement of thermal radiation at a frequency which is the same as that of specularly reflected sunlight; comprising:
    a photometer for detecting radiation at said frequency which arrives along a selected arrival path; and discriminating means cooperating with said photometer to discriminate the polarized from the unpolarized components of the total radiation observed, and producing a processed output signal at least approximating said unpolarized component, said discriminating means comprising:
    a linear polarizing filter interposed in front of said photometer;
    calculating means calculating the position of the plane of incidence of reflected sunlight as a function of the time and place of observation;
    means responsive to said calculating means for maintaining the polarization axis of said filter parallel to said plane of incidence; and
    means for maintaining the attitude of said photometer so that it sights along a path of reflection from a target area at the Brewster angle relative to an estimated index of refraction of the surface of said target area, whereby the radiation sensed by said photometer is substantially only the parallel polarized component of thermal radiation;
    said calculating means being responsive to said photometer to calculate a total thermal radiation value equal to twice the parallel polarized component thereof.

2. A method for daytime measurement of thermal radiation at a frequency which is the same as that of specularly reflected sunlight; comprising the steps of:
    observing radiation at said frequency which arrives along a selected arrival path; and
    discriminating the polarized from the unpolarized components of the total radiation observed by:
    interposing a linear polarizing filter in said arrival path of said observed radiation;
    calculating the position of the plane of incidence of reflected sunlight as a function of the time and place of observation;
    maintaining the polarization axis of said filter parallel to said plane of incidence;
    observing only radiation arriving along a path of reflection from a target area at the Brewster angle relative to an estimated index of refraction of the surface of said target area whereby said radiation is substantially only the parallel polarized component of thermal radiation; and
    calculating a total thermal radiation value equal to twice the parallel polarized component thereof.

3. A device for daytime thermal imaging at a frequency which is the same as that of specularly reflected sunlight; comprising:
    means for constructing an image from a picture element scanned across an image area, the instantaneous brightness of said picture element depending upon the instantaneous amplitude of an input signal received by said image construction means;
    a photometer for detecting radiation at said imaging frequency which arrives along a selected arrival path;
    means for scanning said photometer across a target area in synchronism with said image construction scan;
    discriminating means cooperating with said photometer to discriminate the polarized from the unpolarized components of the total radiation observed, and producing a processed output signal at least approximating said unpolarized component; and
    means connecting said processed output signal as said input signal to said image construction means.

4. A method for daytime thermal imaging at a frequency which is the same as that of specularly reflected sunlight; comprising the steps of:
    constructing an image from a picture element by scanning across an image area;
    observing radiation at said imaging frequency which arrives along a selected arrival path;
    scanning said selected arrival path across a target area in synchronism with said image construction scan;
    discriminating the polarized from the unpolarized components of the total radiation observed; and
    making the instantaneous brightness of said picture element at least approximately proportional to the instantaneous intensity of said unpolarized component.

* * * * *

UNITED STATES PATENT AND TRADEMARK OFFICE
CERTIFICATE OF CORRECTION

PATENT NO. : 4,257,106

DATED : March 17, 1981

INVENTOR(S) : Siegfried O. Auer

It is certified that error appears in the above-identified patent and that said Letters Patent are hereby corrected as shown below:

Column 3, line 65: "varnishes" should read --vanishes--

Column 8, line 37: "the fact" should read --that fact--.

Signed and Sealed this

Sixth Day of October 1981

[SEAL]

Attest:

GERALD J. MOSSINGHOFF

Attesting Officer

Commissioner of Patents and Trademarks